United States Patent

Henry

[11] Patent Number: 5,453,445
[45] Date of Patent: Sep. 26, 1995

[54] LIDOCAINE-PHENYLEPHRINE AEROSOL PREPARATION

[76] Inventor: Richard A. Henry, 7 Toronto Street, Kingston, Ontario, Canada, K7L 4A3

[21] Appl. No.: 236,408

[22] Filed: May 2, 1994

[51] Int. Cl.$^6$ .................. A61K 31/16; A61K 31/135; A61L 9/04
[52] U.S. Cl. .................. 514/626; 424/45; 514/653; 222/635
[58] Field of Search .................. 424/45; 514/626, 514/653; 222/635

OTHER PUBLICATIONS

CA 105: 197096b, Omray, Jul. 1986.
The Merck Index, 11th ed., Dec. 1989, No. 7257, phenyl-ephrine hydrocholoride.
Remington's Pharmaceutical Sciences, 18th ed., Sep. 1990, p. 1706.
Jeffrey Gross et al., Anesthesia & Analgesia 63: 915–918 (Feb. 1984).
Curtis N. Sessler et al., Anesthesiology 64: 274–277 (Jul. 1986).
Robert M. Middleton et al., Chest 99:5 1093–1096 (Oct. 1991).
CPS 25th Edition 1991 (Compendium of Pharmaceuticals and Specialties, Canadian Pharmaceutical Society), p. 406.

*Primary Examiner*—Kimberly R. Jordan
*Attorney, Agent, or Firm*—Whitham, Curtis, Whitham & McGinn

[57] ABSTRACT

An aerosol-dispensable pharmaceutical composition consisting essentially of a combination of lidocaine free base, a pharmacologically-acceptable phenylephrine acid addition salt, and a pharmacologically-acceptable organic solvent, all dissolved in a propellant selected from the group consisting of 1,1,1,2-tetrafluoroethane of the formula $CF_3CH_2F$ (HFC-134a) and 1,1,1,2,3,3,3-heptafluoropropane of the formula $CF_3CHFCF_3$ (HFC-227) or a combination of the said propellants, suitable for dispensing by means of a metered-dosage valve canister in which it is contained under pressure, avoids the necessity of premixing individual solutions by the physician just prior to use. The phenylephrine salt is preferably the hydrochloride and the solvent is preferably ethanol although other pharmacologically-acceptable solvents and pharmacologically-acceptable acid addition salts of phenylephrine may be employed. The lidocaine free base assists in solubilizing the phenylephrine salt and maintaining it in solution in the propellant.

5 Claims, No Drawings

LIDOCAINE-PHENYLEPHRINE AEROSOL PREPARATION

BACKGROUND OF THE INVENTION

Field of Invention

The vasoconstricting agent phenylephrine in acid addition salt form is combined with a particular local anaesthetic, lidocaine base, and dissolved in a solvent and then in a selected HFC propellant to produce a stable solution suitable for metered dose aerosol delivery.

Prior Art

Vasoconstriction of blood vessels is achieved by stimulation of the alpha receptors in the smooth muscle cells of the blood vessel wall. Vasoconstriction is desirable in some clinical situations both systemically to correct hypotension and locally to reduce regional blood flow. The alpha-1 adrenergic receptors, found in the smooth muscle cells of the peripheral vasculature of the coronary arteries, skin, uterus, intestinal mucosa and splanchnic beds, mediate vasoconstriction. These receptors serve as postsynaptic activators of vascular and intestinal smooth muscle as well as endocrine glands. Their activation results in either decreased or increased tone, depending upon the effector organ. The response in resistance and capacitance blood vessels is constriction.

Phenylephrine is considered a potent pure alpha agonist drug which increases venous as well as arterial constriction. Phenylephrine is used intravenously in small doses of 1μg/kg to cause systemic vasoconstriction and elevation of blood pressure. It is also used regionally to cause vasoconstriction when injected with local anaesthetic agents to provide prolonged nerve conduction block.

Phenylephrine has been found to provide excellent decongestion of the nasal mucosa by exerting its alpha-1 mediated vasoconstricting effect on the mucosal blood vessels. This directly opposes the histamine-mediated vasodilation and reduces mucosal edema and vascularity. Other agents that have been used for this effect are ephedrine and cocaine.

Cocaine possesses both anaesthetic and vasoconstricting properties. These properties make it suitable to provide both topical anaesthesia and vasoconstriction of the nasal mucosa to improve patient tolerance of nasal catheterization during nasotracheal intubation, nasogastric tube insertion, or fiberoptic examination of the nose. Vasoconstriction results in shrinking of the nasal mucosa with enlargement of the nasal passage and reduced bleeding during nasal procedures.

Although cocaine provides good vasoconstriction and is well tolerated by most patients, there are significant problems with its use. One such problem is that even small doses (30mg) may cause systemic toxicity and another problem relates to the potential diversion and illicit use of cocaine by medical personnel. The handling and storage of controlled substances involves additional administrative costs and risks.

Lidocaine is similar to cocaine in effectiveness as a local anaesthetic, but it does not vasoconstrict the mucosa and thus dilate the nasal passage. For this reason, phenylephrine is often combined with lidocaine to reduce nasal congestion. The combination of lidocaine and phenylephrine has been advocated as an alternative to cocaine and its efficacy evaluated in a number of studies.

Currently, lidocaine and phenylephrine are required to be mixed by the clinician before applying the solution. Suitable recommended combinations are 3–4% lidocaine hydrochloride in water mixed with 0.25–1% phenylephrine hydrochloride, also in water. The aqueous solution is then delivered to the nasal mucosa as a spray using a conventional manual atomizer or a multi-orificed cannula and syringe delivery system. The optimum dose used with this spray application is 1.25–1.5 mg phenylephrine hydrochloride and 12–15 mg lidocaine hydrochloride per nostril of adult patients.

The methods of delivery and efficacy of lidocaine and phenylephrine are discussed and evaluated in the following studies:

Curtis N. Sessler et. al., Anesthesiology 64: 274–277 (1986); Jeffrey Gross et. al., Anesthesia & Analgesia 63: 915–918 (1984); and Robert M. Middleton et. al., Chest 99:5: 1093–1096 (1991).

Drug deposition in the nasal cavity is reviewed in Volume 39 of the "Drugs and the Pharmaceutical Sciences" series titled Nasal Systemic Drug Delivery, edited by Yie W. Chien, Kenneth S. E. Su and Shyi-Feu Cheng and published by Marcel Dekker, Inc. in 1989.

"The deposition of aerosols in the respiratory tract is a function of particle size and respiratory patterns. The density, shape and hygroscopicity of the particles and the pathological conditions in the nasal passage will influence the deposition of particles, whereas the particle size distribution will determine the site of deposition and affect the subsequent biological response in experimental animals and man."

"A uniform distribution of particles throughout the nasal mucosa could be achieved by delivering the particles from a nasal spray using a pressurized gas propellant."

Factors related to the dosage form of the drug found to affect the pharmacokinetics of nasal absorption are listed:

a) concentration of active drug b) physicochemical properties of active drug c) density/viscosity properties of the formulation d) pH/toxicity of dosage form e) pharmaceutical excipients used Highly concentrated drugs which are lipid soluble at nasal pH of 5.5 to 6.6 and, when dissolved in a minimal amount of excipient, will be rapidly and extensively absorbed.

Lidocaine base is freely lipid soluble and will cross mucous membranes readily. It is insoluble in water and thus not suitable for use in an aqueous suspension, requiring ethanol or the like to obtain a liquid solution. Some way to produce a fine spray of lidocaine base would be advantageous for delivery to the nose.

Phenylephrine base is also lipid soluble, but this molecule is unstable and rapidly oxidizes to phenylephrine oxide. For this reason the more stable water-soluble hydrochloride or bitartrate salts are preferred for clinical use.

Metered dose inhalers (MDI) have been used extensively and have proven to be an effective means of producing a reproducible preselected dose of medicament in a predictable spray pattern and droplet size. This is particularly advantageous when delivering potent drugs where the need for reliable drug delivery is important and where overdosage leads to dangerous clinical side-effects. A problem with the use of MDIs relates to the chlorofluorocarbon (CFC) propellants which have been used to date. All chlorine-containing halohydrocarbons have been implicated in the destruction of the earth's ozone layer with subsequent adverse effects on human and animal life.

A class of propellants referred to as hydrofluorocarbons has been reintroduced for use and will completely replace the CFC propellants by 1996. These agents have zero Ozone Depletion Potential and are not Volatile Organic Compounds (VOC), i.e., they have negligible photochemical reactivity.

Hydrofluorocarbons 1,1,1,2-tetrafluoroethane ($CF_3CH_2F$) HFC-134a and 1,1,1,2,3,3,3-heptafluoropropane ($CF_3CHFCF_3$) HFC-227 have been the subject of extensive toxicological testing over the last few years. Both are soon expected to be approved for use in delivery of medicaments to humans in metered dose aerosol form.

A major problem with both of these propellants is their poor solubility characteristics, making formulations of solutions and suspensions of medicaments in these propellants very difficult. Difficulty in finding suitable cosolvents and surfactants to promote stable suspensions of medicaments in these HFC propellants is slowing development of new aerosol formulations and threatens to prolong the period of phasing out of the CFC propellants.

Most of the metered dose formulations using the HFC propellants are suspensions of finely ground medicament with the use of surfactant agents like oleic acid, sorbitan trioleate and soya lecithin (e.g., isoproterenol-phenylephrine CFC aerosol of Riker/3M - Duomedihaler®).

The object of aerosolized medication delivery is to provide the medicament in stable suspension and preferably solution form in the propellant in a suitable concentration for clinical effect, with minimal or no additives. The droplet size is predictable and is a function of the suspended particle size as well as the relative volume of drug and its cosolvents to the propellant volume. The propellant should constitute at least about 45% of the total formulation weight and preferably about 50–95% of the formulation weight.

Lidocaine and phenylephrine have been shown to exert independent effects on the nasal mucosa that result in vasoconstriction and topical anaesthesia. Both of these effects have been found to be helpful during procedures involving manipulation or examination of the nose. The clinical effect is similar and considered superior in efficacy to cocaine but the need to premix the solution and also to provide a suitable way to deliver a solution or suspension thereof has prevented their combined use from gaining universal acceptance as well as from being employed for all nasal manipulations such as nasogastric tube insertion, where its use would clearly be advantageous to the patient.

Other clinical situations where a combined lidocaine-phenylephrine formulation, preferably in the form of a metered dose aerosol spray of lidocaine base and phenylephrine salt to provide topical anaesthesia and vasoconstriction, could advantageously be used include delivery to the upper airway, open skin wounds, the urethra, anus, and the cervix and vagina.

The present invention provides a solution to this long-standing shortcoming or deficiency of the art.

OBJECTS OF THE INVENTION

An object of the invention is to provide a novel formulation of lidocaine and phenylephrine salt suitable for and/or in metered dose aerosol form. It is a further object to provide a formulation embodying lidocaine in its lipid-soluble free base form to improve absorption and solubility of the phenylephrine salt in the propellant. It is an additional object to provide such compositions incorporating phenylephrine as a stable pharmacologically-acceptable acid addition salt, e.g., the hydrochloride or bitartrate salt, dissolved in a suitable solvent such as anhydrous ethyl alcohol (ethanol). It is another object to incorporate in such compositions only certain selected HFC propellants in accordance with concerns related to use of CFC propellants and ozone depletion. Still further objects will become apparent as this description proceeds and yet additional objects will be apparent to one skilled in the art.

SUMMARY OF THE INVENTION

What I therefore believe and claim to be my invention, inter alia, singly or in combination, is as follows:

An aerosol-dispensable pharmaceutical composition consisting essentially of a combination of lidocaine free base, a pharmacologically-acceptable phenylephrine acid addition salt, and a pharmacologically-acceptable organic solvent, all dissolved in a propellant selected from the group consisting of 1,1,1,2-tetrafluoroethane of the formula $CF_3CH_2F$ (HFC-134a) and 1,1,1,2,3,3,3-heptafluoropropane of the formula $CF_3CHFCF_3$ (HFC-227) or a combination of the said propellants; such a composition wherein the amount of solvent is between that amount sufficient to dissolve the phenylephrine salt and about 50% w/w, the amount of lidocaine free base is about 1–20% w/w, the amount of phenylephrine acid addition salt is about 0.1–2% w/w, and the amount of propellant is about 45%–95% w/w; such a composition wherein the amount of solvent is about 5–40% w/w, the amount of lidocaine free base is about 5–20% w/w, the amount of phenylephrine acid addition salt is about 0.25–2% w/w, and the amount of propellant is about 50%–80% w/w; such a composition wherein the solvent is ethanol and the phenylephrine acid addition salt is the hydrochloride; such a composition wherein the amount of phenylephrine hydrochloride is about 1% w/w; and such a composition wherein the solvent is selected from the group consisting of ethanol, polypropylene glycol, polyethylene glycol, diethylether, and dimethoxyethane.

Moreover, such a composition under pressure in a metered-dosage valve canister which dispenses about 25–100 microliters per metered dosage, preferably 25 or 50 microliters per unit dosage; such a composition wherein the amount of lidocaine free base dispensed per metered dosage unit dispensed is about 1–20 mg and the amount of phenylephrine acid addition salt dispensed per metered dosage unit is about 0.05–1 mg; such a composition wherein the amount of lidocaine free base dispensed per metered dosage unit is between about 1 and 10 mg, and the amount of phenylephrine acid addition salt dispensed per unit dose is between about 0.1 and 1 mg; such a composition wherein the amount of lidocaine free base dispensed per metered dosage unit is about 2.5–5 mg, and the amount of phenylephrine acid addition salt dispensed per metered dosage unit is about 0.1–0.5 mg; such a composition wherein the solvent is ethanol and the phenylephrine acid addition salt is the hydrochloride; and such a composition wherein the amount of lidocaine free base dispensed per metered dosage unit is about 2.5–5 mg and the amount of phenylephrine hydrochloride is about 0.2 mg and the ethanol solvent is about 30% w/w.

THE INVENTION IN GENERAL

The present invention relates to lidocaine free base and a pharmacologically-acceptable phenylephrine acid addition salt, e.g., the hydrochloride or bitartrate, in a solution as a formulation suitable for aerosol delivery together with one or more of certain specified HFC propellants.

Phenylephrine hydrochloride is water soluble and was found to be insoluble in propellants HFC-134a and HFC-227. Moreover, when dissolved in ethyl alcohol in clinically useful concentrations and then mixed with HFC-134a or 227, the phenylephrine hydrochloride was precipitated out of solution in the alcohol.

Lidocaine base has surprisingly been found to be extremely soluble in the HFC propellants of interest. See Table.

| Solubility of Lidocaine in Selected Propellants | | |
|---|---|---|
| | Solubility | |
| Propellant | Weight % | mg/ml |
| Dymel ® 134a $CF_3CH_2F$ | 58 | 759 |
| FM 200 ® $CF_3CHFCF_3$ | 45 | 602 |
| Water | Ins. | — |

When lidocaine base was added to the crystalline phenylephrine hydrochloride and the mixture then added to propellant HFC-134a or 227, the phenylephrine hydrochloride did not dissolve. However, again surprisingly, when phenylephrine hydrochloride was dissolved in ethyl alcohol and admixed with lidocaine base before the addition of HFC 134a or 227, or vice versa, the phenylephrine remained in solution in the resulting formulation. The lidocaine free base obviously acts as an adjuvant to assist and maintain the solubility of the phenylephrine salt.

The formulation of this invention is therefore lidocaine base with a phenylephrine acid addition salt, preferably the hydrochloride, dissolved in a suitable solvent such as ethyl alcohol in solution in HFC-134a or HFC-227 or a combination thereof.

DETAILED DESCRIPTION OF THE INVENTION

The formulation of the present invention and suitable for topical nasal anaesthesia and vasoconstriction is free base lidocaine plus phenylephrine hydrochloride or other acid addition salt, dissolved in anhydrous ethyl alcohol or other suitable solvent, in solution in the selected non-CFC hydrofluorocarbon propellant HFC-134a (1,1,1,2-tetrafluoroethane: $CF_3CH_2F$) or HFC-227 (1,1,1,2,3,3,3-heptafluoropropane; $CF_3CHFCF_3$) or a combination thereof, preferably under pressure in a predetermined metered-dosage-releasing aerosol delivery container.

Lidocaine USP in free base form, of the formula 2-(Diethylamino)-2',6'-acetoxylidide [137-58-6] $C_{14}C_{22}N_2O$ (MW 234.34), was obtained from Astra Pharmaceuticals, Inc. in Mississuaga, Ontario, Canada.

Phenylephrine hydrochloride of the formula (R)-3-Hydroxy-alpha-[(methylamino)methyl]benzenemethanol hydrochloride $C_9H_{14}ClNO_2$ (MW 203.67) was obtained from Sigma Chemicals.

The aerosol propellants employed are HFC-134a, available from E. I. du Pont de Nemours and Company under their Trademark Dymel 134a ($CF_3CH_2F$), and HFC-227 ($CF_3CHFCF_3$), supplied by Great Lakes Chemical under their Trademark FM 200.

Both propellants are a nonflammable vapor at room temperature and atmospheric pressure. Neither contains chlorine atoms and, as such, neither are implicated in stratospheric ozone destruction by chlorofluorocarbons or other chlorinated hydrocarbons.

Phenylephrine hydrochloride crystalline, both alone and in combination with lidocaine, was determined to be insoluble in both of the propellants employed.

PROCEDURE

The general procedure employed was as follows:

Phenylephrine hydrochloride was dissolved in ethyl alcohol (ethanol) to produce a 2.5% w/w solution. This solution was placed in a glass bottle designed for pressure filing with liquid propellant. When HFC-134a was added to this solution, the phenylephrine hydrochloride was precipitated out of solution. Then, using the same phenylephrine hydrochloride in ethanol solution, lidocaine free base was added. With the addition of HFC-134a under pressure, the lidocaine went into solution in the 134a as expected, but it also served to place and keep the phenylephrine hydrochloride in solution. HFC-227 acted the same. The following Examples are given by way of illustration only and are not to be construed as limiting.

Example 1

| | | |
|---|---|---|
| Phenylephrine hydrochloride | 43 mg | 0.86% w/w |
| Lidocaine free base | 350 mg | 7.0% w/w |
| Ethanol (density 0.81 g/ml) | 1650 mg | 33.0% w/w |
| HFC-134a (density 1.22 g/ml) | 2957 mg | 59.14% w/w |

Example 2

| | | |
|---|---|---|
| Phenylephrine hydrochloride | 25 mg | 0.5% w/w |
| Lidocaine free base | 500 mg | 10.0% w/w |
| Ethanol | 1000 mg | 20.0% w/w |
| HFC-134a | 3475 mg | 69.5% w/w |

Example 3

| | | |
|---|---|---|
| Phenylephrine hydrochloride | 40 mg | 0.8% w/w |
| Lidocaine free base | 1000 mg | 20.0% w/w |
| Ethanol | 1550 mg | 31.0% w/w |
| HFC-134a | 2410 mg | 48.2% w/w |

Example 4

| | | |
|---|---|---|
| Phenylephrine hydrochloride | 32 mg | 0.64% w/w |
| Lidocaine free base | 320 mg | 6.4% w/w |
| Ethanol | 1600 mg | 32.0% w/w |
| HFC-227 | 3048 mg | 60.96% w/w |

The solutions of all examples are advantageously useful and effective for their intended purpose.

Formulations incorporating other pharmacologically-acceptable organic solvents and other pharmacologically acceptable phenylephrine acid addition salts are equally operative and give utilizable solutions.

Thus, the possibility of a combination of lidocaine and phenylephrine salt, e.g., the hydrochloride, in a stable solution in the selected HFC propellant, suitable for topical delivery to the nose, was discovered and has now been realized. This formulation provides lidocaine in lipid-soluble base form and phenylephrine as a stable salt, preferably the hydrochloride, and dissolved in a suitable organic solvent, preferably anhydrous and preferably ethyl alcohol, in combination with one of the non-CFC propellants HFC-134a or HFC-227 or combinations thereof.

Other suitable pharmacologically-acceptable organic solvents may be used to place the phenylephrine salt, e.g., bitartrate or hydrochloride, into solution such as propylene glycol, polyethylene glycol, diethylether, and DME (dimethoxyethane or ethylene glycol dimethyl ether-Monoglyme®). These solvents, as well as ethanol, serve additionally as a valve lubricant, preventing a metered-dose valve from sticking during use. Higher concentrations of solvent, e.g., ethanol, may also be used and will produce and maintain a solution, but the less solvent the better both from a most effective concentration and a most effective aerosol particle size standpoint.

Preferably about 1–20% weight/weight (w/w) of lidocaine free base and 0.1–2% w/w of phenylephrine salt, hydrochloride or bitartrate, in e.g. anhydrous ethyl alcohol, are employed to provide about 1–20 mg lidocaine and 0.05–1mg of phenylephrine salt, e.g., hydrochloride, per metered dose.

This combination under pressure in a canister with a 25–100, usually 25–50, and preferably about 25 microliter metered dose valve and appropriate intranasal delivery catheter or other device representatively releases 25–50 microliters of solution per metered dose. This most preferably provides 1–10 mg lidocaine and 0.1–1 mg phenylephrine hydrochloride or other pharmacologically-acceptable acid addition salt per metered dose.

The preferred combination is preferably chosen to limit the solvent and preferably ethanol to a maximum of about 35% and preferably 33% w/w to limit nasal irritation and ensure small enough droplet size to achieve adequate intranasal dispersion. A concentration of about 5–40%, preferably 15–35% w/w, and especially about 30% solvent, e.g., ethanol, w/w is considered optimal. This limitation on solvent, e.g., ethanol, limits the amount of phenylephrine hydrochloride able to be dissolved but still allows an ideal therapeutic dose of 0.1–1 and preferably 0.1–0.5 mg per metered dose to be realized.

The high solubility of lidocaine base in the selected HFC propellants allows a wide range of concentrations and dosages to be achieved. In the therapeutic concentrations considered desirable, lidocaine free base unpredictably enables solubility of the phenylephrine salt, e.g., the hydrochloride, and keeps it in solution in the HFC propellant employed.

The present formulation of lidocaine free base and a phenylephrine salt in aerosol form is also useful for delivery to the airway (specifically epiglottis, larynx and trachea), open wounds (broken skin), and other mucosal structures such as the urethra, prostatic urethra, bladder, anus, cervix, and vagina. The formulation of the present invention is moreover well adapted for all of its uses and applications in the field of veterinary medicine as will immediately be recognized by one skilled in the art.

It is therefore seen from the foregoing that a novel and valuable solution of a pharmacologically-acceptable acid addition salt of phenylephrine and lidocaine free base and a pharmacologically-acceptable solvent in a selected non-CFC propellant, namely, HFC-134a or HFC-227 or a combination thereof, which is suitable for aerosol application, has been provided, thereby remedying an obvious shortcoming in the art. The acid addition salt of phenylephrine is preferably the hydrochloride or the bitartrate and the solvent employed is preferably ethyl alcohol, although other salts and other solvents may be employed with facility as described in the foregoing. As already set forth in the foregoing, the amount of solvent employed is that amount which is required to place the phenylephrine acid addition salt into solution and the maximum amount of solvent present in the composition of the invention may be as great as 50% w/w but is optimally about 15–40% w/w and preferably about 30% w/w and in any event an excess of solvent over that amount required to place the phenylephrine acid addition salt into solution is not recommended, inasmuch as it reduces the concentration of active ingredients and makes it more difficult to place effective amounts of solution into maximally-effective small-sized aerosol spray particles, e.g., 5–25 microns in size, when the amount of solvent employed is greater than necessary.

The amount of lidocaine free base in the composition of the invention is between about 1 and 20% w/w, preferably between about 5 and 20% w/w. Per unit dose as administered in spray form and preferably by means of an aerosol spray as set forth hereinbefore, the amount of lidocaine is usually between about 1 and 20 mg per dose, preferably between about 1 and 10 mg per dose, and optimally about 2.5–5 mg per dose.

Correspondingly, the amount of phenylephrine acid addition salt in the composition is between about 0.1 and 2% w/w, preferably between about 0.25 and 2% w/w, and optimally about 1% w/w. Per unit dose, especially when administered by aerosol but also when administered by simple spray device, the dose of phenylephrine acid addition salt administered is usually between about 0.05 and 1 mg per unit dose, preferably between about 0.1 and 0.5 or 1.0 mg per unit dose, and optimally about 0.2 mg per unit dose.

For optimal aerosol delivery, the amount of the aerosol propellant HFC-134a or HFC-227 should be between about 50% and 95% w/w and, as indicated by the foregoing examples, percentages of about 60% w/w for HFC-227 and 50–70% w/w for HFC-134a are quite satisfactory.

With the combination composition of the invention under pressure in a canister with a metered dose valve providing between about 25 and 100 microliters per metered dose, usually between about 25 and 50 microliters per unit dose, and most preferably about 25 microliters per metered dose, no problem is encountered in delivering effective amounts of the phenylephrine acid addition salt and the lidocaine free base in sufficiently small aerosol particle size and in accord with and within the foregoing enumerated dosage ranges. Numerous metered-dosage delivering canisters of the type employed are readily available in the art, for example, the one employed with the Riker/3M-Duomedihaler product, or the representative such device disclosed in my U.S. patent application Ser. No. 07/949,445, allowed Mar. 8, 1994.

The advantages of having the phenylephrine acid addition salt and the lidocaine free base available in aerosol form together with a suitable HFC and non-CFC propellant all in solution in a minimal amount of pharmacologically-acceptable solvent and all dissolved in the propellant will be readily appreciated by medical practitioners and others skilled in the art.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

I claim:

1. An aerosol-dispensable pharmaceutical composition consisting essentially of a combination of lidocaine free base in an amount ranging from 5 to 20 % w/w, ethanol in an amount ranging from 5 to 20% w/w, and [the] phenylephrine acid addition salt which is the hydrochloride in an amount ranging from 0.25 to 2% w/w, all dissolved in a propellant selected from the group consisting of 1,1,1,2-tetrafluoroethane and 1,1,1,2,3,3,3-heptafluoropropane and combinations thereof.

2. A composition of claim 1, wherein the amount of phenylephrine hydrochloride is about 1% w/w.

3. An aerosol-dispensable pharmaceutical composition consisting essentially of a combination of lidocaine free base, a pharmacologically-acceptable phenylephrine acid addition salt which is the hydrochloride, and ethanol, all dissolved in a promellant selected from the group consisting of 1,1,1,2-tetrafluoroethane, 1,1,1,2,3,3,3-heptafluoropropane, and combinations thereof, and all under pressure in a metered-dosage valve canister which dispenses said lidocaine free base in an amount ranging from 1 to 10 mg per metered dosage unit, and dispenses said phenylephrine acid addition salt in an amount ranging from 0.1 to 1 mg per metered dosage unit.

4. A composition of claim 3 wherein the amount of lidocaine free base dispensed per metered dosage unit is about 2.5–5 mg and the amount of phenylephrine hydrochloride is about 0.2 mg and the ethanol solvent is about 30% w/w.

5. An aerosol-dispensable pharmaceutical composition; comprising:

lidocaine present at an amount ranging from 15 to 40% w/w;

a phenylephrine acid addition salt which is phenylepherine hydrochloride and is present at an amount ranging from 0.25 to 2% w/w;

an organic solvent which is ethanol and is present in an amount ranging from 15 to 40% w/w; and a propellant which is 1,1,1,2-tetrafluoroethane, said lidocaine and said phenylepemhrine hydrochloride, and said ethanol being dissolved in said 1,1,1,2-tetrafluoroethane.

* * * * *